US010532163B2

(12) United States Patent
Kleyman et al.

(10) Patent No.: US 10,532,163 B2
(45) Date of Patent: Jan. 14, 2020

(54) FLUID DISPENSING DEVICE

(71) Applicants: Gennady Kleyman, Brooklyn, NY (US); Alexander Merson, Brooklyn, NY (US); Oleg Shikhman, Trumbull, CT (US)

(72) Inventors: Gennady Kleyman, Brooklyn, NY (US); Alexander Merson, Brooklyn, NY (US); Oleg Shikhman, Trumbull, CT (US)

( * ) Notice: Subject to any disclaimer, the term of this patent is extended or adjusted under 35 U.S.C. 154(b) by 109 days.

(21) Appl. No.: 15/632,254

(22) Filed: Jun. 23, 2017

(65) Prior Publication Data

US 2018/0001032 A1    Jan. 4, 2018

Related U.S. Application Data

(60) Provisional application No. 62/357,952, filed on Jul. 2, 2016.

(51) Int. Cl.
*A61M 5/315* (2006.01)
*A61M 5/31* (2006.01)

(52) U.S. Cl.
CPC .... *A61M 5/31578* (2013.01); *A61M 5/31501* (2013.01); *A61M 2005/3126* (2013.01); *A61M 2205/581* (2013.01); *A61M 2205/582* (2013.01)

(58) Field of Classification Search
CPC .......... A61M 5/31501; A61M 5/31595; A61M 2005/31508
See application file for complete search history.

(56) References Cited

U.S. PATENT DOCUMENTS

| 1,110,189 | A | | 9/1914 | Dodge |
| 2,474,496 | A | * | 6/1949 | Rayman ............ A61M 5/31555 604/210 |
| 2006/0184136 | A1 | | 8/2006 | Kleyman et al. |
| 2007/0265579 | A1 | | 11/2007 | Kleyman et al. |
| 2011/0172640 | A1 | | 7/2011 | Cronenberg et al. |
| 2016/0058953 | A1 | | 3/2016 | Marano, Jr. |
| 2016/0144122 | A1 | | 5/2016 | Locati et al. |

OTHER PUBLICATIONS

PCT Search Report for PCT Application PCT/US2017/039140 dated Sep. 15, 2017.
Galderma Syringe from Les Techniques Skinboosters Oct. 23, 2014.

* cited by examiner

*Primary Examiner* — Emily L Schmidt
(74) *Attorney, Agent, or Firm* — Neil D. Gershon

(57) ABSTRACT

A fluid dispensing device having a barrel having a lumen for containing a fluid therein and a flexible structure extending from the barrel. A plunger is axially slidable within the lumen to dispense fluid from the barrel, the plunger having a first set of grooves spaced apart a first distance and a second set of grooves spaced apart a second distance. The flexible structure includes a flexible arm extending transversely with respect to the barrel and configured to engage the grooves.

9 Claims, 9 Drawing Sheets

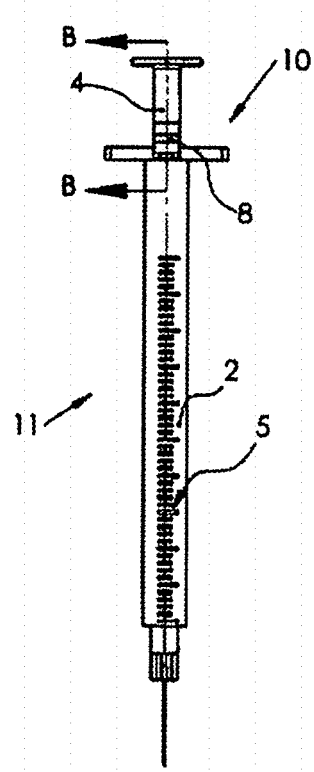
FIG. 1
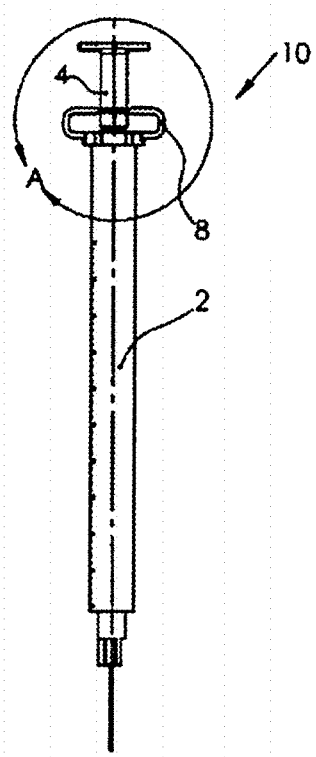
FIG. 2
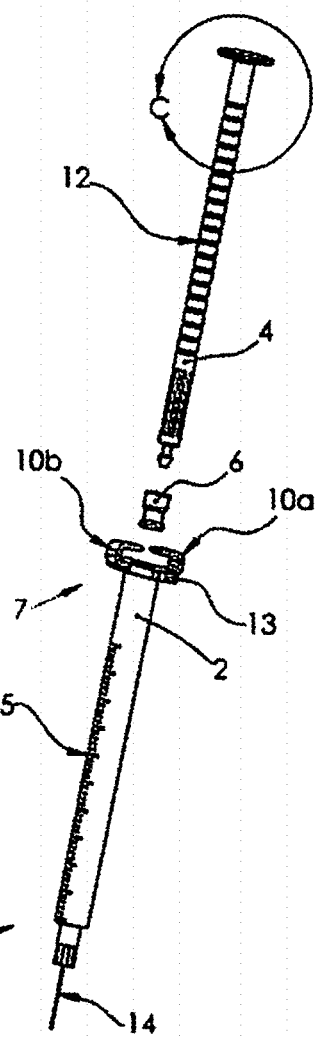
FIG. 3
FIG. 4
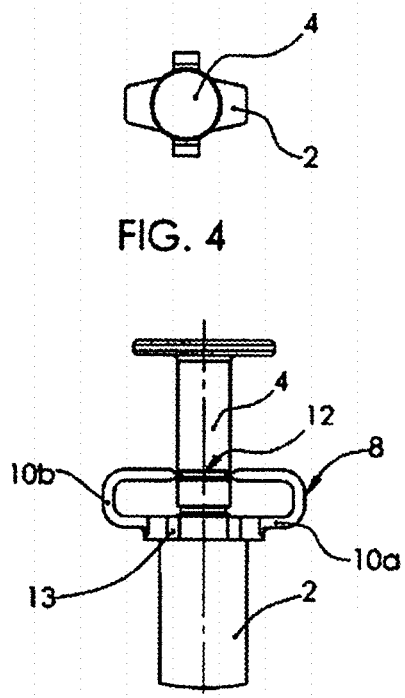
FIG. 5
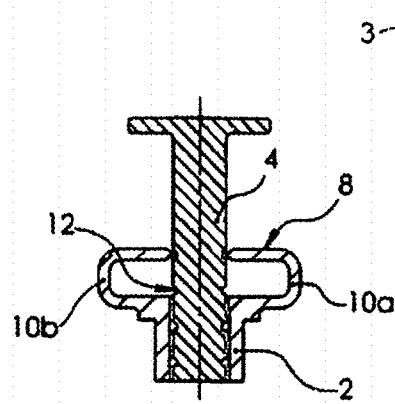
FIG. 6
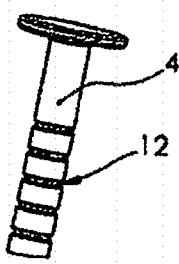
FIG. 7

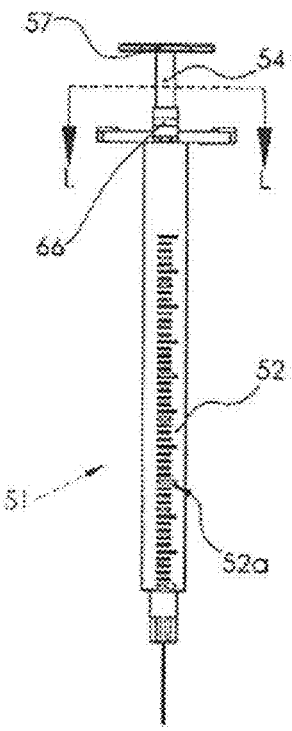
FIG. 25
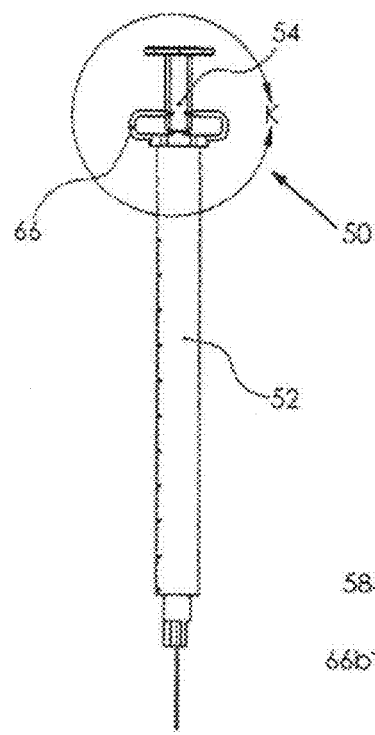
FIG. 26
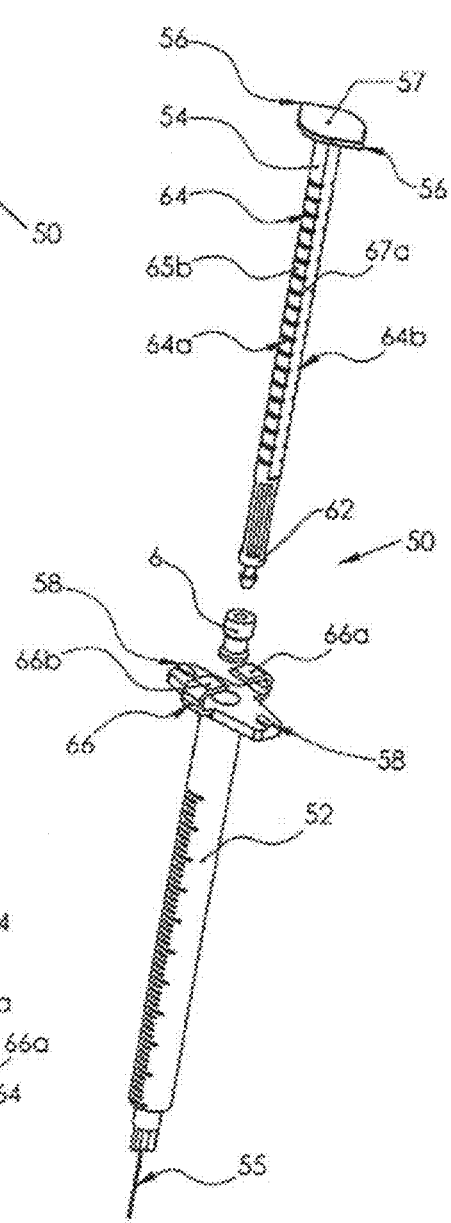
FIG. 28
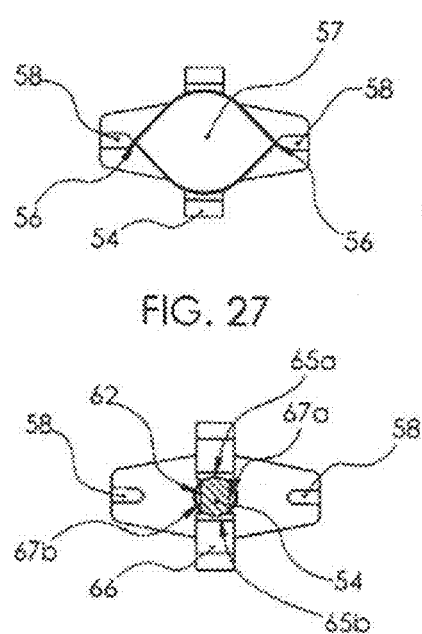
FIG. 27
FIG. 29
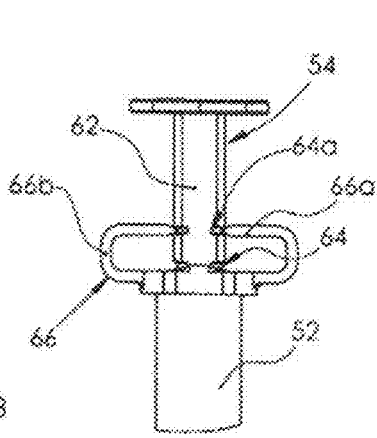
FIG. 30

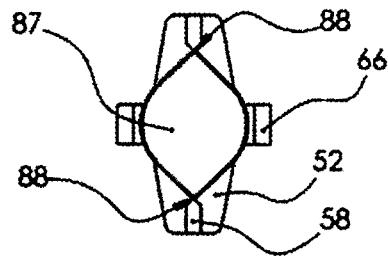
FIG. 44
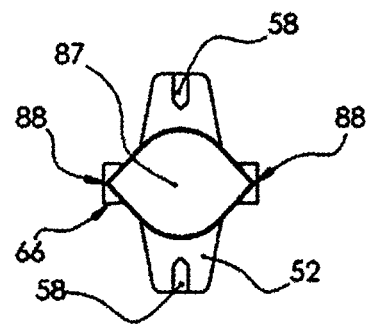
FIG. 45
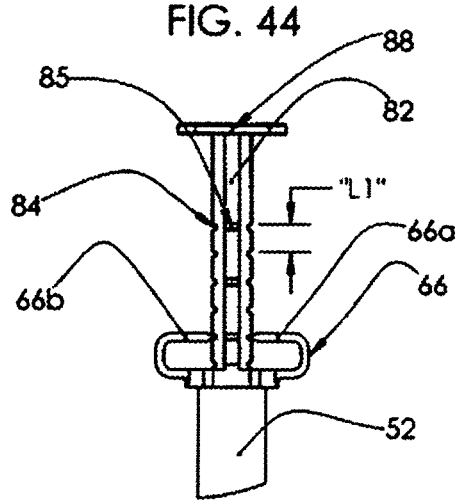
FIG. 46
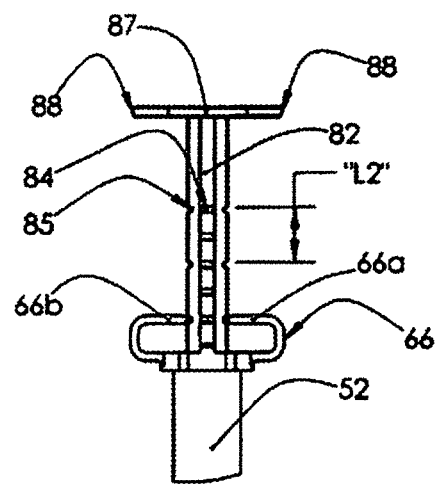
FIG. 47
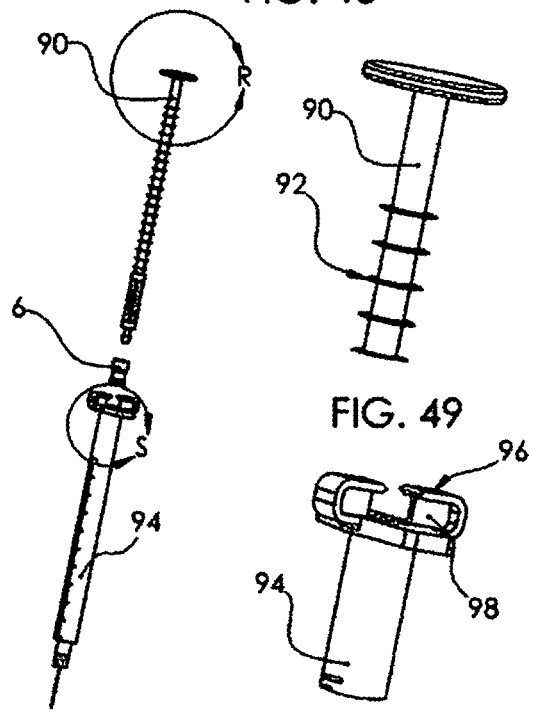
FIG. 48
FIG. 49
FIG. 50
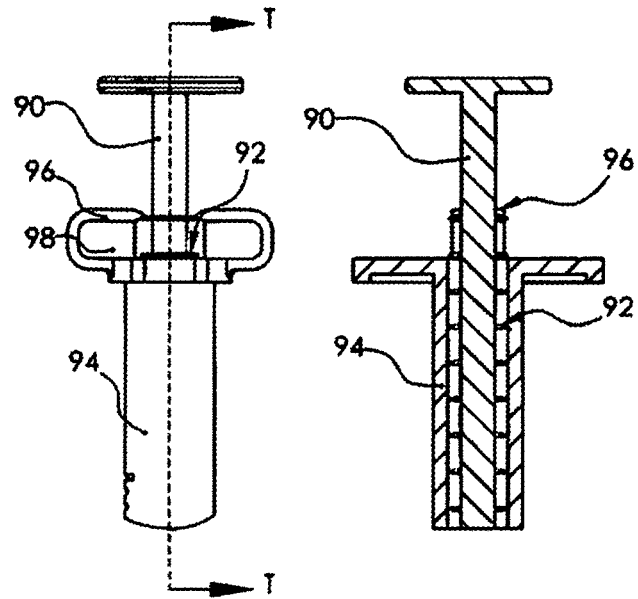
FIG. 51
FIG. 52

FLUID DISPENSING DEVICE

This application claims priority from provisional application 62/357,952, filed Jul. 2, 2016, the entire contents of which are incorporated herein by reference.

BACKGROUND

Technical Field

This application relates to a fluid dispensing device, and, more particularly, to a fluid dispensing device for supplying select doses of fluid.

Background of Related Art

Devices for drawing and administering predetermined amounts or dosages of fluid are widely used in a variety of industries including, but not limited to, medicine. Dosage devices, such as hypodermic syringes, administer the drug directly in the bloodstream or in the tissue of the patient, who is thus directly affected by the drug. As a result, it is very important to assure that the precise dosage is administered at all times.

Commonly, hypodermic syringes include a graduated scale disposed on the body of the syringe. Utilizing the scale, an individual administering a drug will draw a quantity of the drug from a vial into the syringe, and then expel quantities of the drug until the precise dosage is achieved. This common measurement procedure can often be difficult and time-consuming, and more importantly, can be quite wasteful, as a quantity of the drug is often discarded in order to achieve the appropriate dosage. Other syringes are provided to hospitals or clinicians pre-filled. Still, the user relies on the scale or markings on the syringe to deliver the appropriate doses.

Quite often, medical professionals administering an injection may not have a clear view of the targeted body part of the patient. In this case, many rely on their experience to administer the desired dosage, which still may not be precise. Furthermore, those individuals who self-administer drugs may experience even more inconvenience that the professionals. Diminished hearing, eyesight and/or diminished dexterity of the user may lead individuals to draw or dispense an imprecise dosage of the drug into, or from the syringe. More significantly, it may lead them to draw or dispense an insufficient or excessive dosage into their body, which can result in life-threatening or worse, fatal, consequences.

Attempts have been made in the prior art to overcome these problems and provide some type of structure, which allows a person to accurately transfer the amount of medication to and from a syringe.

U.S. Pat. No. 4,252,159 to Maki teaches a dosage device including an elongated slat body on which a syringe is mounted by means of upstanding substantially Y-shaped brackets that are spaced from one another and extend upwardly from a flat exposed surface of the body. An adjustable top member threadedly engages an upstanding internally threaded element provided with externally located lands that, in turn, co-operate with an irregularly shaped knob so as to produce audible signals upon 360° revolution. The engagement and sound between the above-mentioned elements depends upon a number of factors which may include flexibility of the base or play between the threaded engagement such that the outwardly projected portion of the knob may pass over and in engagement with the lands.

U.S. Pat. No. 4,466,426 to Blackman discloses a syringe that has a plunger providing an audible sound upon a plunger being withdrawn from the barrel of a syringe.

U.S. Pat. No. 4,883,101 to Strong discloses a device for filling an injection syringe which incorporates a sound indicator provided with mechanical, electrical or an electronic sound device. A spring-loaded ball bearing is biased against a gear wheel and produces a distinctly audible clicking sound when the gear moves a single notch. A user counts the sounds accurately indicating the amount of liquid medicine drawn into the syringe when the attached syringe holder moves.

U.S. Pat. Nos. 5,741,232 and 5,795,333 to Reilly disclose a front loading syringe having a movable plunger rotatable on an injector housing. An audible indicating mechanism is activated when the syringe is essentially in the desired mounted position and includes ribs which function as volumetric gradations.

While the above noted patents are all directed to structures which attempt to overcome problems associated with dispensing proper dosage of medicine, these structures are rather complicated and inconvenient in use. The need therefore arises to have a simple structure of a dosing device that will allow a user to administer medicine in a simple and efficient manner.

Furthermore to minimize the aforementioned inconveniences, some of the known dosage devices have been provided with a tactile mechanism operative to generate a sound signal and/or increased resistance indicating displacement of the desired dosage of fluid into and from the dosage device.

U.S. Pat. Nos. 6,579,269 and 7,901,384 disclose syringes which attempt to provide a structure configured to reliably produce a distinct audible and tactile signal to the user indicating that the desired dosage of fluid has been drawn into, or displaced from, the dosage devices in a reliable, simple fashion. Although these patents disclose such signals to indicate dosage increments, their versatility is limited. This adds to the expense of the syringes and limits the manufacturer's ability to provide varied assortment of syringes tailored to applying predetermined or carefully controlled amounts of fluid.

It would be advantageous to provide syringes which facilitate adaptation to varied dosage needs in an efficient, reliable and cost effective way.

SUMMARY

The present invention provides in one aspect a fluid dispensing device having a barrel having a lumen for containing a fluid therein and a flexible structure extending from the barrel. A plunger is axially slidable within the lumen to dispense fluid from the barrel, the plunger having a first set of grooves spaced apart a first distance and a second set of grooves spaced apart a second distance. The flexible structure includes a flexible arm extending transversely with respect to the barrel and positioned to engage either the first set of grooves or the second set of grooves.

In accordance with another aspect, the present invention provides a fluid dispensing device comprising a barrel having a lumen for containing a fluid therein, a flexible structure extending from the barrel, and a plunger axially slidable within the lumen to dispense fluid from the barrel. The plunger has a first set of grooves and a second set of grooves and a first position wherein the flexible structure is engageable with grooves of the first set of grooves when the plunger is advanced through the barrel and a second position wherein the flexible structure is engageable with grooves of the second set of grooves when the plunger is advanced through the barrel.

In accordance with another aspect of the present invention a fluid dispensing device is provided comprising a barrel having a lumen for containing a fluid therein, a flexible structure extending from the barrel and a plunger axially slidable within the lumen to dispense fluid from the barrel. The plunger has a first wall having a first set of grooves, a second wall having a second set of grooves, and a third wall between the first and second walls. The plunger has a first orientation and a second orientation, wherein a) in the first orientation the flexible structure is engageable with the first set of grooves and the second set of grooves when the plunger is advanced axially within the barrel and b) in the second orientation the flexible structure is not engageable with the first set of grooves or the second set of grooves when the plunger is advanced axially through the barrel.

In accordance with another aspect, the present invention provides a fluid dispensing device comprising a barrel having a lumen for containing a fluid therein and a flexible structure extending from the barrel, the flexible structure having a first arm and a second arm, and a plunger axially slidable within the lumen to dispense fluid from the barrel. The plunger has a first wall having a first set of grooves spaced apart a first distance and a second wall having a second set of grooves spaced apart a second distance different than the first distance, the first arm having a first stiffness and the second arm having a second stiffness. The first arm is engageable with the first set of grooves and the second arm is engageable with the second set of grooves, wherein the first arm provides feedback to the user different than feedback provided by the second arm.

In accordance with another aspect, the present invention provides a fluid dispensing device comprising a barrel having a lumen for containing a fluid therein and a plunger axially slidable within the lumen to dispense fluid from the barrel, the plunger having an asymmetrical transverse cross-sectional dimension having a first wall and a second wall. The first wall has a first set of grooves spaced apart a first distance and the second wall has a second set of grooves spaced apart a second distance different than the first distance. A flexible structure is mountable to the barrel and has a first arm and is mountable to the barrel in a select orientation so that the first arm is engageable with either the first set of grooves or the second set of grooves.

In accordance with another aspect, the present provides a fluid dispensing device comprising a barrel having a lumen for containing a fluid therein and a deflectable structure extending from the barrel and a plunger axially slidable within the lumen to dispense fluid from the barrel, the plunger having a longitudinal axis and a set of grooves extending longitudinally along an outer surface. The deflectable structure extends transversely with respect to the barrel and positioned to engage the set of grooves and deflects in a transverse direction to disengage from the grooves.

In accordance with another aspect of the present invention, a fluid dispensing device is provided comprising a barrel having a lumen for containing a fluid therein and a deflectable structure extending from the barrel, the deflectable structure including first and second arms, wherein the first arm has a first proximal surface and the second arm has a second proximal surface. The first and second arms are spaced apart so that the first and second proximal surfaces are not contiguous. A plunger is axially slidable within the lumen to dispense fluid from the barrel and has a longitudinal axis and a set of grooves extending longitudinally along an outer surface. The first and second arms extend transversely with respect to the barrel and positioned to engage the set of grooves.

In accordance with another aspect, the present invention provides a fluid dispensing device comprising a barrel having a lumen for containing a fluid therein and a deflectable structure extending from the barrel, the deflectable structure including a first arm having a first proximal portion and a first distal portion. A plunger is axially slidable within the lumen to dispense fluid from the barrel, the plunger having a longitudinal axis and a set of grooves extending longitudinally along an outer surface. The deflectable structure extends transversely with respect to the barrel and positioned to engage the set of grooves, wherein the first arm is configured such that the distal portion deflects to a greater degree than the proximal portion as the first flexible arm disengages from the groove.

In accordance with another aspect, the present invention provides a fluid dispensing device comprising a barrel having a lumen for containing a fluid therein and a deflectable structure extending from the barrel, the deflectable structure including a first arm having a first proximal portion and a first distal portion. A plunger is axially slidable within the lumen to dispense fluid from the barrel, the plunger having a longitudinal axis and a set of grooves extending longitudinally along an outer surface. The deflectable structure extends transversely with respect to the barrel and positioned to engage the set of grooves, wherein the distal portion and the proximal portion of the first arm are deflectable as the first arm disengages from the groove.

In accordance with another aspect, the present invention provides a fluid dispensing device comprising a barrel having a lumen for containing a fluid therein and a flange. A plunger is axially slidable within the lumen to dispense fluid from the barrel, the plunger having a longitudinal axis and a set of grooves extending longitudinally along an outer surface. A deflectable structure is mountable to the proximal portion of the barrel and is engageable with an underside of the flange, the deflectable structure extending transversely with respect to the barrel and positioned to engage the set of grooves, the deflectable structure being external of the barrel and exposed.

In accordance with another aspect, the present invention provides a kit for dispensing fluid comprising a) a plunger positioned within a barrel containing a fluid therein, the plunger having an asymmetrical cross-sectional dimension having a first wall and a second wall, the first wall having a first set of grooves spaced apart a first distance and the second wall having a second set of grooves spaced apart a second distance different than the first distance, and b) a mounting structure slidable over the plunger and mountable to the barrel, the mounting structure having a flexible member for engagement with one of the sets of grooves during advancement of the plunger to dispense fluid.

In accordance with another aspect, the present invention provides a method of assembling a syringe comprising:

mounting a plunger within a barrel, the plunger having at least one set of grooves extending along an exterior surface;

sliding a mounting structure over the plunger, the mounting structure including a flexible arm configured for engagement with the grooves of the plunger during axial advancement of the plunger;

attaching the mounting structure to the barrel; and mounting a pressing surface onto a proximal end of the plunger.

In accordance with another aspect, the present invention provides a method for delivering select doses of fluid to a patient comprising:

providing a fluid dispensing device having a barrel and a plunger slidable axially within a lumen of the barrel, the plunger having a first set of grooves and a second set of grooves;

selecting the set of grooves to be engaged by a flexible element of the fluid dispensing device; and advancing the plunger such that the flexible element engages the grooves of the selected set of grooves thereby providing feedback for fluid delivery of an amount corresponding to a distance between the grooves of the selected set of grooves.

BRIEF DESCRIPTION OF THE DRAWINGS

Preferred embodiment(s) of the present disclosure are described herein with reference to the drawings wherein:

FIG. 1 is a front view of one embodiment of the fluid dispensing device (syringe) of the present invention;

FIG. 2 is a side view of the fluid dispensing device of FIG. 1; FIG. 3 is an exploded perspective view of the fluid dispensing device of FIG. 1;

FIG. 4 is a top view of the fluid dispensing device of FIG. 1;

FIG. 5 is a detailed view of the indicated area A of FIG. 2;

FIG. 6 is a cross-sectional view taken along line B-B of FIG. 1;

FIG. 7 is a detailed view of the indicated area C of FIG. 3;

FIG. 25 is a front view of another alternate embodiment of the fluid dispensing device of the present invention;

FIG. 26 is a side view of the fluid dispensing device in the position of FIG. 25;

FIG. 27 is a top view of the fluid dispensing device in the position of FIG. 25;

FIG. 28 is an exploded perspective view of the fluid dispensing device of FIG. 25;

FIG. 29 is a cross-sectional view taken along line L-L of FIG. 25;

FIG. 30 is a detailed view of the indicated area K of FIG. 26;

FIG. 44 is a top view of the fluid dispensing device of FIG. 40 showing the plunger in line with the barrel tabs for engagement of the flexible arms of the feedback mechanism with a first set of plunger grooves;

FIG. 45 is a top view of the fluid dispensing device of FIG. 40 showing the plunger tabs perpendicular to the barrel tabs for engagement of the flexible arms of the feedback mechanism with a second set of plunger grooves;

FIG. 46 is a side view of the proximal portion of the plunger and barrel in the plunger position of FIG. 44;

FIG. 47 is a side view of the proximal portion of the plunger and barrel in the plunger position of FIG. 45;

FIG. 48 is an exploded view of another alternate embodiment of the fluid dispensing device of the present invention;

FIG. 49 is a detailed view of the indicated area R of FIG. 48;

FIG. 50 is a detailed view of the indicated area S of FIG. 48;

FIG. 51 is a front view of the proximal portion of the device of FIG. 48;

FIG. 52 is a cross-sectional view taken along line T-T of FIG. 51;

DETAILED DESCRIPTION OF PREFERRED EMBODIMENTS

Figure 8:
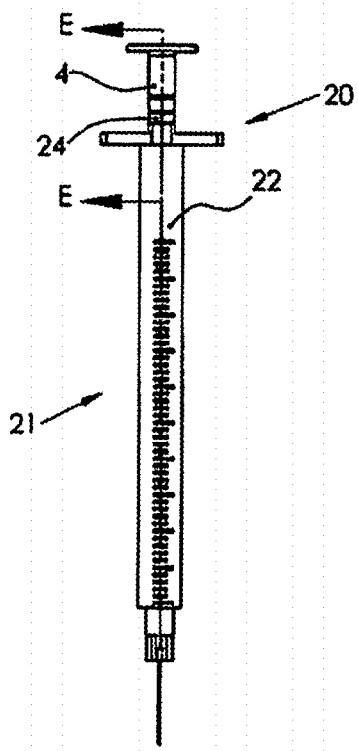
FIG. 8 is a front view of an alternate embodiment of the fluid dispensing device of the present invention.
Figure 9:
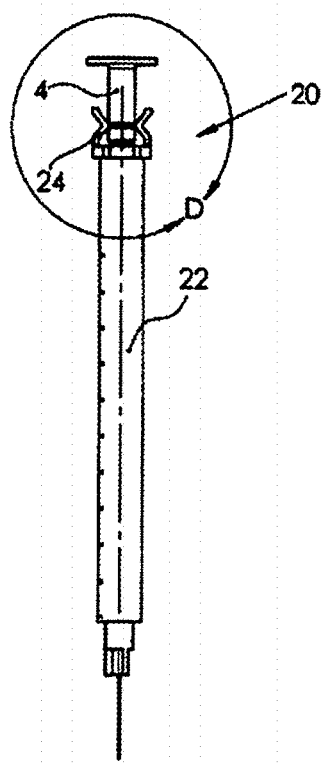
FIG. 9 is a side view of the fluid dispensing device of FIG. 8.
Figure 10:
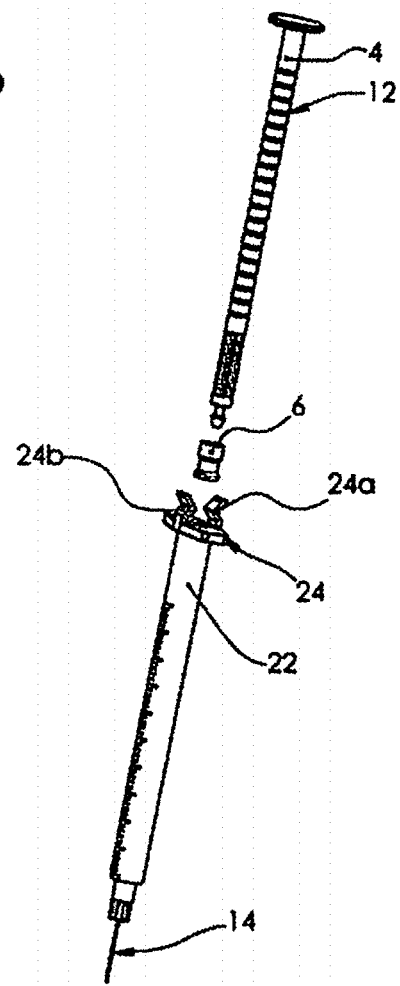
FIG. 10 is an exploded perspective view of the fluid dispensing device of FIG. 8.
Figure 11:
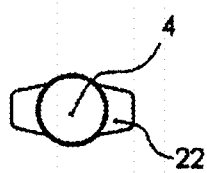
FIG. 11 is a top view of the fluid dispensing device of FIG. 8.
Figure 12:
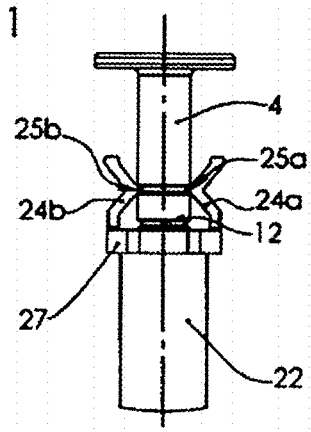
FIG. 12 is a detailed view of the indicated area D of FIG. 9.
Figure 13:
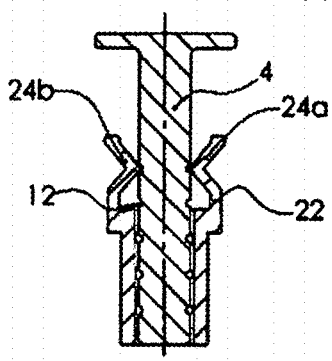
FIG. 13 is a cross-sectional view taken along line E-E of FIG. 8.
Figure 14:
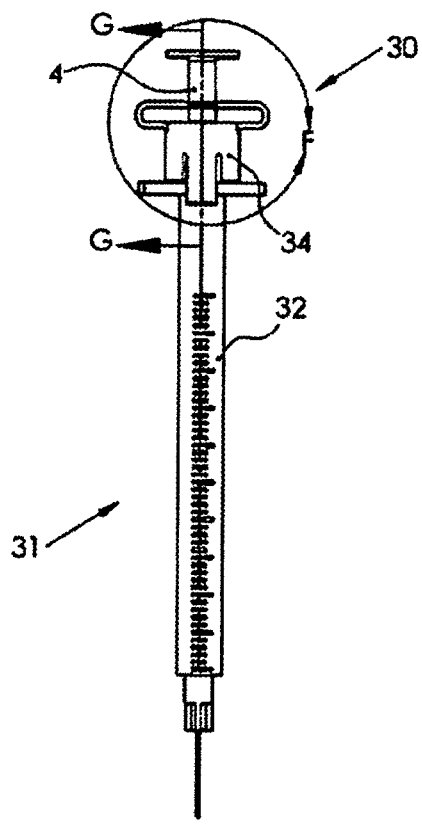
FIG. 14 is a front view of another alternate embodiment of the fluid dispensing device of the present invention.
Figure 15:
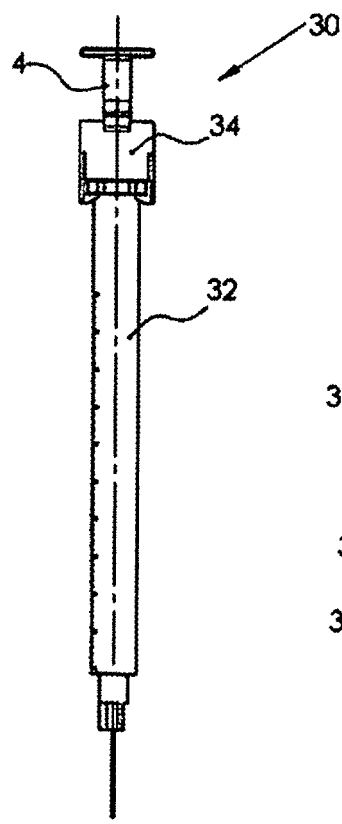
FIG. 15 is a side view of the fluid dispensing device of FIG. 14.

The present invention is directed to fluid dispensing devices that provide feedback to the user to enable incremental delivery of a fluid from the fluid dispensing device. The devices of the various embodiments disclosed herein include a barrel containing the fluid, a plunger axially slidable within the barrel to deliver the fluid from the barrel and a feedback mechanism to indicate to the user the progression of the plunger within the barrel and the doses of fluid administered. The feedback mechanism provides a tactile and/or an audible indicator to the user to enable effective advancement of the plunger in increments to provide desired doses of fluid from the barrel, and better control of such incremental fluid delivery. In some embodiments, the barrel is formed with the plunger engaging mechanism which provides the feedback mechanism; in other embodiments the plunger engaging mechanism is attached to a standard barrel. In either of these versions, modularity is provided to decrease the cost of manufacture and enable standard syringes to be easily modified to add on the feedback mechanism of the present invention.

Additionally, to accommodate the user's desire to select optimal delivery doses, in some embodiments disclosed herein, the feedback mechanism is designed to provide varied doses within a single syringe. Various exemplary embodiments are discussed below.

As used herein, the term proximal refers to regions closer to the user and the term distal refers to regions further from the user. Further, the terms fluid dispensing device and syringe are used interchangeably. The fluids that can be administered include gels for cosmetic surgeries, insulin, therapeutic agents such as chemotherapy agents, and any other injectable fluids.

Turning now to the drawings wherein like reference numerals correspond to the same elements throughout the drawings and turning first to FIGS. 1-7, one embodiment of the dispensing device or syringe is illustrated and designated generally by reference numeral 11. The dispensing device 11 includes a barrel 2, a plunger 4 and a feedback mechanism 10. The barrel 2 includes a lumen formed therein to receive fluid for delivering to a patient and markings 5 along its length to provide a visual indication to the user of the amount of fluid contained within the barrel 2. Penetrating needle 14 extends distally from a distal end 3 of the barrel 2. The plunger 4 is received in barrel 2 for axially slidable movement distally to dispense the fluid from the barrel 2. A plurality of grooves 12 are formed in an outer (external) surface of the plunger 4 along its length, spaced apart at intervals or increments corresponding to the amount of fluid desired to be injected at each step of advancement of the plunger 4 within the barrel 6. The grooves 12 can extend along a partial length or the entire length of the plunger. In the illustrated embodiment, the plunger grooves 12 are equidistantly spaced apart to provide equal doses of fluid. However, it is also contemplated that in alternate embodiments, the spacing between grooves could be non-uniform to accommodate situations where it is desired to provide larger or smaller doses at certain times during injection. Also, the distances between the grooves can be greater or less than the distances shown in the Figures to provide variations on dosage delivery. Examples of spacings between grooves can be 0.1 cc, 0.5 cc, 1 cc, etc. (Such examples can also be used with the other embodiments disclosed herein). Other spacings are also contemplated. The grooves are spaced at intervals corresponding to a predetermined dose of fluid from the barrel. Although the grooves are shown substantially perpendicular to the longitudinal axis of the plunger they can alternatively be placed at other angles to the longitudinal axis.

Feedback mechanism 10 includes a flexible structure 8 having a pair of flexible arms 10a, 10b engageable with plunger grooves 12. Arms 10a, 10b are external of barrel 2. They can be exposed and visible to the user as shown. Arms 10a, 10b extend proximally from a proximal end 7 of the barrel 2 and then bend inwardly toward the longitudinal axis of the device. Thus, the arms 10a, 10b form two somewhat U-shaped members with one leg, i.e., the distal leg, of the U extending transversely from cap or support 13 and the other leg, i.e., the proximal leg, extending transversely toward the longitudinal axis to engage one of the grooves 12 on the plunger 4 and the base of the U extending longitudinally. Thus, the two transverse legs of arms 10a, 10b extend toward one another (and are shown with their ends facing one another) to engage one of the plunger grooves 12. Note the plunger grooves 12 are shown extending circumferentially 360 degrees around the surface of the plunger 4. Thus, engagement of the arms 10a, 10b of the grooves is not dependent on the rotational position of the plunger 4 with respect to the barrel 2. However, it is also contemplated that the grooves can be formed around less than 360 degrees around the outer surface of plunger 4 and can be formed, for example, on opposing surfaces of the plunger 4 such that each groove is engaged by one of the arms 10a, 10b.

The flexible structure 8 of the feedback mechanism 10 is attached to the barrel 2 by various methods such as by welding. In this manner, the flexible structure can be attached to a standard barrel during manufacture rather than requiring designing an entire barrel. That is, the support 13 can be mounted and attached to a proximal end of the standard barrel. Note the flexible structure can be an integral piece or alternatively can be composed of separate attached components such as a cap (support) with openings through which each leg of the separate arm components extend and is attached. Each arm can also be a separate piece attached to the support.

A rubber seal 6 can be provided, inserted into the barrel 2 and positioned to prevent leakage of fluid from the barrel 2. The plunger 4 would extend through seal 6.

The flexible arms 10a, 10b, by engaging a groove 12 of the plurality of grooves, provide a tactile and/or audible indicator of the movement and position of the plunger 4. More specifically, as the plunger 4 is advanced within barrel 2, the arms 10a, 10b engage one of the grooves 12. Application of sufficient distal force on the plunger 4 will override the arm/groove engagement so the plunger 4 can be further advanced to the next groove. This continues so the plunger can be advanced step by step, i.e., in increments, with each step indicated to the user by one or both of a tactile feel and an audible sound such as by a clicking noise as the arms 10a, 10b click into the groove 12. It should be appreciated that not only can the increments be adjusted by varying the distance between grooves 12 as discussed above, but the force required to advance the plunger 4 and thus the degree of tactile feedback (and audible feedback) can also be adjusted. The force can be affected by the depth of the grooves, the flexibility of the arms 10a, 10b, the material of the arms 10a, 10b, the angle of the arms with respect to the plunger grooves 12, or by other ways. For example, if the arms engage deeper grooves more force will be required and will provide increased feedback (both tactile and audible). Less flexible arms and more rigid material will also require more force and thus provide increased feedback. It is also contemplated that the depth of the grooves can vary along the length to provide different degrees of feedback if desired.

Figure 37:
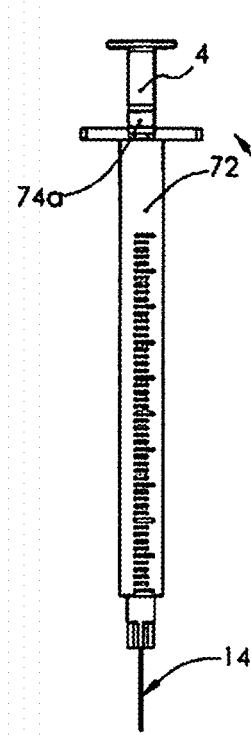
FIG. 37 is a front view of another alternate embodiment of the fluid dispensing device.
Figure 38:
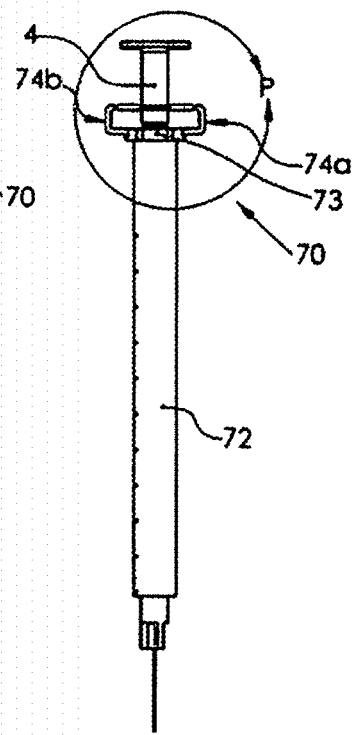
FIG. 38 is a side view of the fluid dispensing device of FIG. 37.
Figure 39:
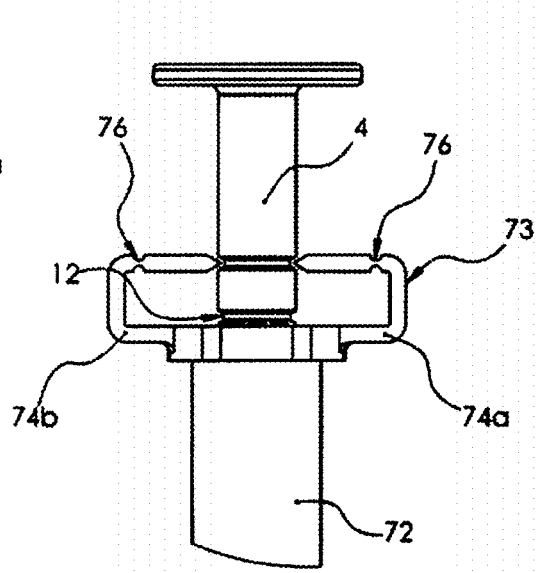
FIG. 39 is a detailed view of the indicated area P of FIG. 38.

A specific example of arm modification to adjust the force required to advance the plunger is shown, in the embodiment of FIGS. 37-39 wherein the arms 74a, 74b of flexible structure 73 have a cutout 76 to increase flexibility. This reduces the force requirement. Note more than one cutout could be provided to further increase the flexibility. In all other respects, e.g., plunger 4 and barrel 72, the fluid dispensing device 71 is identical to the fluid dispensing device 11 of the embodiment of FIG. 1 and therefore for brevity, further discussion of the components is not provided since the description of the components and their function with regard to the embodiment of FIGS. 1-7 is fully applicable to the embodiment of FIGS. 37-39.

Turning back to FIGS. 1-7, in use, the user would remove from the package the syringe 11 which would contain the flexible structure 8 of the feedback mechanism 10 already attached. The barrel 2 can be prefilled or require filling after removal from the packaging. The user then advances the plunger 4 distally within the barrel 2 until the user feels a stop and/or hears a click. The physical stop felt by the user (as well as the click) is a result of engagement of the arms 10a, 10b with one of the grooves 12. To dispense more fluid, the user advances the plunger 4 further distally, forcing the arms 10a, 10b out of engagement with the groove 12 and sliding the plunger 4 until the arms 10a, 10b engage the next plunger groove 12. This dispenses the next amount of fluid, i.e., corresponding to the distance between the two grooves. This continues until the user has delivered the desired amount of fluid from the syringe 11.

FIG. 8-13 illustrate an alternate embodiment of the fluid dispensing device (syringe) of the present invention. The fluid dispensing device 21 is the same as fluid dispensing device 11 of FIGS. 1-7 except for the configuration of the flexible structure of the feedback mechanism. Therefore, dispensing device 11 has a plunger 4, plunger grooves 12 formed in the plunger 4, needle 14 and seal 6 identical to that of fluid dispensing device 11 of FIGS. 1-7. Therefore, for brevity, further discussion of these components is not provided herein since the description of these components and their function with respect to dispensing device 11 of FIGS. 1-7 is fully applicable to dispensing device 21 of FIGS. 8-13. As noted above, device 21 differs from device 11 in the feedback mechanism 20.

Flexible structure 24 of feedback mechanism 20 is attached to barrel 22 in manufacture by various methods such as welding. Flexible structure 24 includes a pair of flexible elements or arms 24a, 24b. In the illustrated embodiment, the arms 24a, 24b extend from a cap or support 27 which is attached in manufacture to a proximal end of barrel 22 so the arms are external and proximal of barrel 22. Flexible arms 24a, 24b are V-shaped, the vertex of the V extending toward the longitudinal axis of the barrel 22. More specifically, the arms 24a, 24b have a longitudinal component extending proximally from a cap or support (base) 27 at a proximal end portion of the barrel 22, then angle inwardly to a vertex 25a, 25b, respectively, than angle outwardly away from the longitudinal axis. The inward angle toward and away from the vertex as shown is about 40 degrees, however, other angles are also contemplated. The vertices 25a, 25b of arms 24a, 24b engage one of the grooves 12 of the plunger 4. The vertices 25a, 25b extend toward one another (and are shown with their ends facing one another) to engage one of the plunger grooves 12. Thus, the arms 24a, 24b can be considered V-shaped with a distal arm angled proximally inwardly and the proximal arm angled distally inwardly to a vertex. In an alternate embodiment, the arms 24a, 24b can be more U-shaped to have more curved arms and a vertex with more curvature. Note the plunger grooves 12 are shown extending circumferentially 360 degrees around the surface of the plunger 4. Thus, engagement of the arms 24a, 24b of the grooves is not dependent on the rotational position of the plunger 4 with respect to the barrel 2. However, it is also contemplated that the grooves can be formed on less than 360 degrees around the outer surface of plunger 4 and can be formed, for example, on opposing surfaces of the plunger 4 such that each groove is engaged by one of the arms 24a, 24b.

The arms 24a, 24b, by engaging a groove of the plurality of grooves 12 provide a tactile and/or audible indicator of the movement and position of the plunger 4. More specifically, as the plunger 4 is advanced within barrel 22, the arms 24a, 24b engage one of the grooves 12 as the vertices 25a, 25b engage the groove 12. Application of sufficient force on the plunger 4 will override the arm/groove engagement so the plunger 4 can be further advanced to the next groove. This continues so the plunger 4 can be advanced step by step, i.e., in increments, with each step indicated to the user by a tactile feel and/or by an audible indicator such as by a clicking noise. It should be appreciated that as with the embodiment of FIG. 1 (as well as the other embodiments discussed herein) the increments can be adjusted by varying the distance between grooves 12. Thus, the distance between the grooves can be greater or less than shown in the illustrated embodiments to provide greater or less increments for delivery or larger or smaller doses of fluid. Additionally, as with the embodiment of FIG. 1 discussed above (as well as the other embodiments discussed herein), the force required to advance the plunger 4 and thus the degree of tactile feedback can also be adjusted. The force can be affected in various ways such as by the depth of the grooves, the flexibility of the arms 24a, 24b, the material of the arms 24a, 24b, the angle of the arms, 24a, 24b, e.g., the angle of the V emanating from the vertex 25a, 25b, etc. Note the arms could have an undercut (or additional cuts/removed material) to improve flexibility (as in the embodiment of FIG. 37) formed for example in a distal arm or in the longitudinal component of the arms.

In use, the user would remove from the package the syringe 21 which would contain the flexible structure 24 of the feedback mechanism 20 already attached to the barrel 20. The barrel 20 can be prefilled or require filling after removed from the package. The user then advances the plunger 4 distally within the barrel 22 until the user feels a stop and/or hears a click. The physical stop felt by the user is a result of engagement of the arms 24a, 24b with one of the grooves 12. To dispense more fluid, the user advances the plunger further distally, forcing the arms 24a, 24b (i.e., the vertices 25a, 25b) out of engagement with the groove until they engage the next plunger groove. This dispenses the next amount of fluid, i.e., an amount in accordance with the distance between the two grooves. This continues until the user has delivered the desired amount of fluid from the syringe 21.

The configuration of the flexible structures disclosed herein, e.g., flexible arms 10a, 10b and 25a, 25b, enhance flexibility to facilitate fine increments of advancement. This is achieved based on one or more factors. One factor is the arms are separated so that a proximal surface of the arms are not contiguous, enabling independent movement of the arms. Additionally, the arms are configured so that both the distal portion and the proximal portion of the arm flex to provide more flexibility as the arms are disengaged from the groove. Additionally, in preferred embodiments, a distal portion of the arms flexes to a greater degree than the proximal portion as the arms are disengaged from the groove, i.e., the deflection point (weaker portion) is closer to the barrel. The arms in the disclosed embodiments deflect in a transverse direction (sideways action) rather than in an up and down direction to disengage from the groove. This results in the arms engaging the groove as soon as it is aligned with the groove to provide a more efficient ratchet type mechanism. It should also be appreciated in some embodiments a single arm rather than multiple arms can be utilized.

As noted above, the embodiments of FIGS. 1-13 provide a fluid dispensing device where the flexible structure of the feedback mechanism can be formed with the barrel. In the alternate embodiments of FIGS. 14-24, the feedback mechanism is snap fit or otherwise attached to the barrel. This facilitates manufacture as modular flexible structures can be readily attached to a standard barrel. It is contemplated that the attachment of the feedback mechanism of the embodiment of FIGS. 14-24 to the barrel occurs during manufacture, however, it is also contemplated, in certain embodiments, that the flexible structure of the feedback mechanism can be packaged or provided separately and snap fit or otherwise attached to the barrel by the user post manufacture.

Turning first to the embodiment of FIGS. 14-18, the fluid dispensing device or syringe of this alternate embodiment is designated generally by reference numeral 31. The fluid dispensing device 31 is the same as fluid dispensing device 11 of FIGS. 1-7 except for the flexible structure of the feedback mechanism. Therefore, dispensing device 31 has a plunger 4, plunger grooves 12 formed in the outer surface of plunger 4, needle 14 and seal 6 identical to that of fluid dispensing device 11 of FIGS. 1-7. Therefore, for brevity, further discussion of these components is not provided herein since the description of these components and their function with respect to fluid dispensing device 11 of FIGS. 1-7 is fully applicable to fluid dispensing device 31 of FIG. 14-18.

As noted above, device 31 differs from device 11 in the feedback mechanism 30. Flexible structure (mounting structure) 36 of feedback mechanism 30 is attached to barrel 32 by a snap fit, although other methods are contemplated such as by press fit, glue or ultrasound welding by way of example. Flexible structure 36, like flexible structure 8, has a pair of flexible arms 34a, 34b engageable with plunger grooves 12 as they bend inwardly toward the longitudinal axis of the device. Thus, the two arms 34a, 34b extend transversely toward one another (and are shown with their ends facing one another) to engage one of the plunger grooves 12 in the same manner as arms 10a, 10b of FIGS. 1-7.

Figure 17:
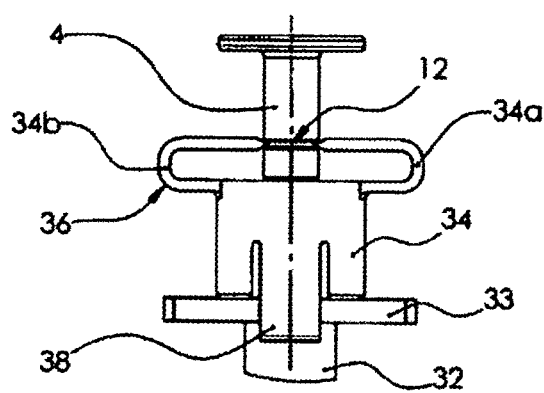
FIG. 17 is a detailed view of the indicated area F of FIG. 14.
Figure 18:
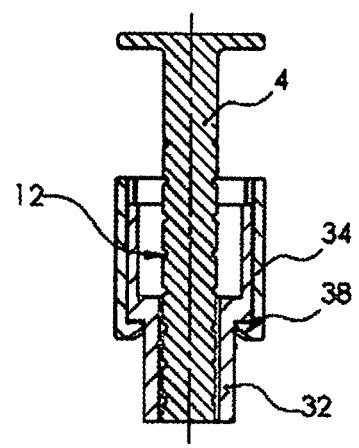
FIG. 18 is a cross-sectional view taken along line G-G of FIG. 14.
Figure 19:
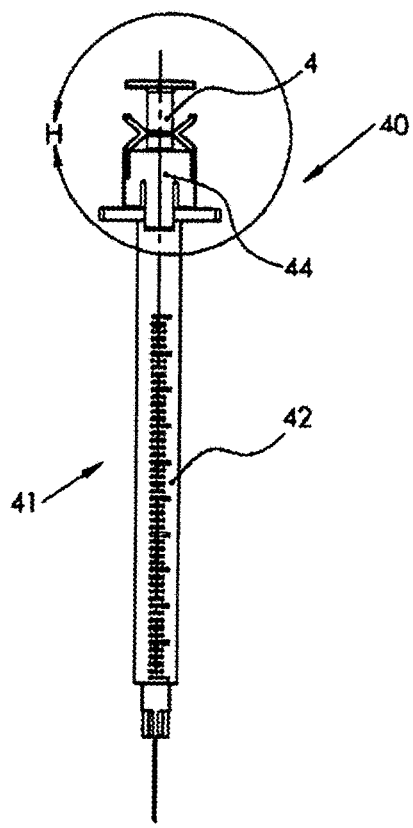
FIG. 19 is a front view of another alternate embodiment of the fluid dispensing device of the present invention.
Figure 20:
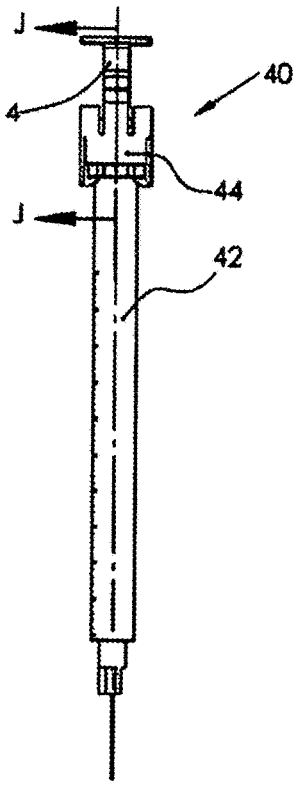
FIG. 20 is a side view of the fluid dispensing device of FIG. 19.
Figure 21:
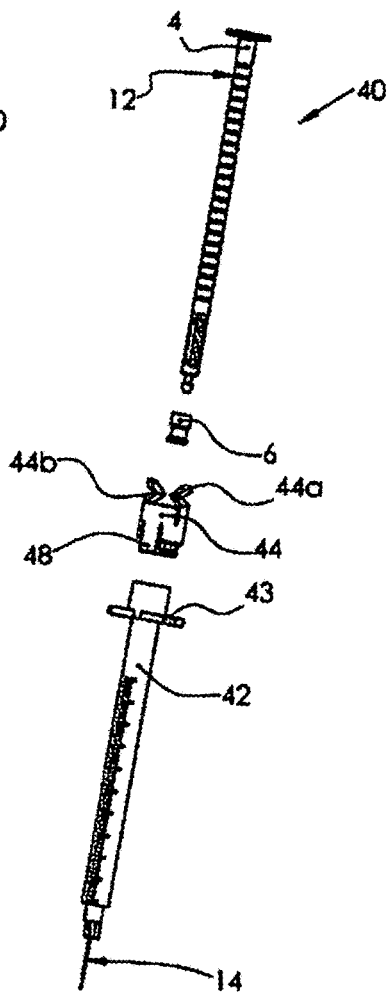
FIG. 21 is an exploded perspective view of the fluid dispensing device of FIG. 19.

The flexible structure 36 differs from flexible structure 8 by the mounting to the barrel 32. More specifically, arms 34a, 34b of flexible structure 36 are somewhat U-shaped members with one leg, i.e., the distal leg, of the U extending longitudinally from support or mounting cap 34, the base of the U extending longitudinally and the other leg, e.g., the proximal leg, extending transversely toward the longitudinal axis to engage one of the grooves 12 on the plunger 4. Support 34 provides a snap attachment as distally extending flexible tabs or grips 38, spaced apart by about 180 degrees to be formed on opposing sides of the support 34, are snapped over proximal flange 33 of barrel 32 and engage an undersurface of flange 33 as shown in FIGS. 17 and 18 to attach flexible structure 36 to the barrel 32. Note flange 33 is at a proximal portion of the barrel 32 spaced distally from the proximalmost edge to provide a cylindrical region over which the feedback mechanism (mounting/deflectable structure) is positioned as it is slid over the proximal end of the barrel 32. With the flange 33 engaged, the feedback mechanism is effectively mounted to barrel 32. Note the mounting can be provided so as to be removable so that the feedback mechanism 30 can subsequently be removed from barrel 32. Alternatively, the mounting can be provided such that once the feedback mechanism 30 is attached to the barrel 32, it cannot be removed. Also note that other feedback mechanisms disclosed herein can be a separate structure with flexible tabs to engage the underside of flange 33 to mount to the barrel 32. Note additional spaced tabs or grips 38 can be provided to snap over flange 33.

Note the plunger grooves 12 are shown extending circumferentially 360 degrees around the surface of the plunger 4. Thus engagement of the arms 34a, 34b of the grooves is not dependent on the rotational position of the plunger 4 with respect to the barrel 32. However, it is also contemplated that the grooves can be formed on less than 360 degrees around the outer surface of plunger 4 and can be formed, for example, on opposing surfaces of the plunger 4 such that each groove is engaged by one of the arms 34a, 34b.

The arms 34a, 44b, by engaging a groove of the plurality of grooves 12 provide a tactile and/or audible indicator of the movement and position of the plunger 4 in the same manner as described above with respect to the embodiment of FIG. 1, i.e., engagement of the arms 34a, 34b with grooves 12. Therefore, for brevity, further discussion of the arm/groove engagement and use of the fluid dispensing device of FIGS. 14-18 will not be provided since the discussion of the arm/groove engagement, the tactile and audible feedback and the use of the device 11 of the embodiment of FIG. 1 is fully applicable to fluid dispensing device 31 of FIGS. 14-17. Additionally, the discussion above of adjustment of the distances between grooves and adjustment of the force to adjust the tactile feedback is fully applicable to the embodiment of FIGS. 14-17.

It should be appreciated that it is contemplated that the flexible structure 34 be attached to the barrel 32 during manufacture. However, it is also contemplated that in certain embodiments the user or clinician (e.g., pharmacist) post manufacture can snap fit (or otherwise attach) the flexible structure 36 to the barrel 32 if desired to provide better controlled incremental advancement or for selective groove engagement in the embodiments discussed below. In such use, the user would remove from the package the flexible structure 36 and if desired attach flexible structure 36 by pressing the structure over the proximal end of the barrel 32 until the flexible tabs 38 bypass and snap under flange 33. Thus, a kit can be provided containing the plunger, barrel and mounting structure, e.g., flexible structure, for attachment to the barrel.

An alternate embodiment of the fluid dispensing device or syringe is illustrated in FIGS. 19-24 and is designated generally by reference numeral 41. The fluid dispensing device 41 is the same as fluid dispensing device 11 of FIGS. 1-7 except for the configuration of the flexible structure of the feedback mechanism. Therefore, dispensing device 41 has a plunger 4, plunger grooves 12 formed in the plunger 4, needle 14 and seal 6 identical to that of fluid dispensing device 11 of FIGS. 1-7. Therefore, for brevity, further discussion of these components is not provided herein since the description of these components and their function with respect to dispensing device 11 of FIGS. 1-7 is fully applicable to dispensing device 41 of FIG. 19-24.

As noted above, device 41 differs from device 11 in the feedback mechanism 40. Flexible (mounting) structure 46 of feedback mechanism 40 is attached to barrel 42 by a snap fit in the manner as described in the embodiment of FIGS. 14-18 (slid over the proximal region of the barrel), although other methods are contemplated such as by press fit, glue or ultrasound welding by way of example. Flexible structure 46, like flexible structure 24 of the embodiment of FIGS. 8-13, has a pair of flexible arms or elements 44a, 44b engageable with plunger grooves 12 as they bend inwardly toward the longitudinal axis of the device. The flexible arms 44a, 44b, like arms 24a, 24b are V-shaped, the vertex of the V extending toward the longitudinal axis of the barrel 42. More specifically, the arms 44a, 44b extend proximally from a cap or support 44, angle inwardly to a vertex 45a, 45b, respectively, than angle outwardly away from the longitudinal axis of feedback mechanism 40. The angle shown is about forty degrees, however, other angles are also contemplated. The vertices 45a, 45b of arms 44a, 44b of feedback mechanism 40 engage one of the grooves 12 of the plunger 4. The vertices 45a, 45b extend toward one another (and are shown with their ends facing one another) to engage one of the plunger grooves 12. Note the plunger grooves 12 are shown extending circumferentially 360 degrees around the surface of the plunger 4. Thus, engagement of the arms 44a, 44b of the grooves is not dependent on the rotational position of the plunger 4 with respect to the barrel 2. However, it is also contemplated that the grooves can be formed less than 360 degrees around the outer surface of plunger 4 and can be formed, for example, on opposing surfaces of the plunger 4 such that each groove is engaged by one of the arms 44a 44b.

Figure 22:
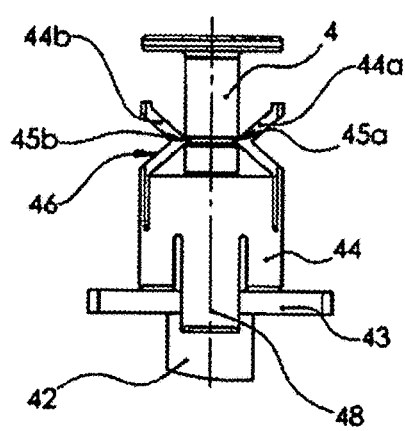
FIG. 22 is a detailed view of the indicated area H of FIG. 19.
Figure 23:
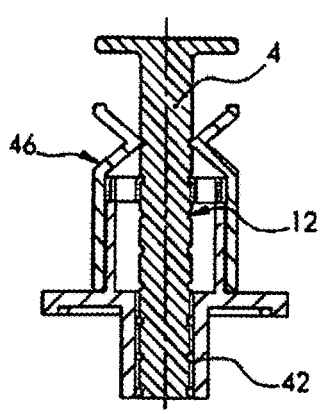
FIG. 23 is a cross-sectional view taken along line J-J of FIG. 20.
Figure 24:
FIG. 24 is a top view of the fluid dispensing device of FIG. 19.
Figure 31:
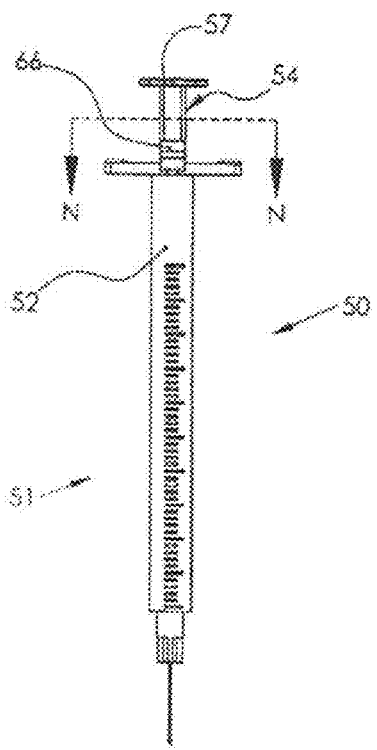
FIG. 31 is a front view similar to FIG. 25 showing the plunger rotated to a second orientation for non-engagement of the plunger grooves.
Figure 32:
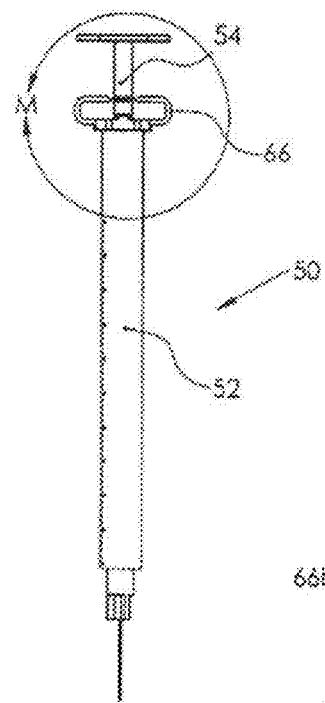
FIG. 32 is a side view of the fluid dispensing device in the position of FIG. 31.
Figure 34:
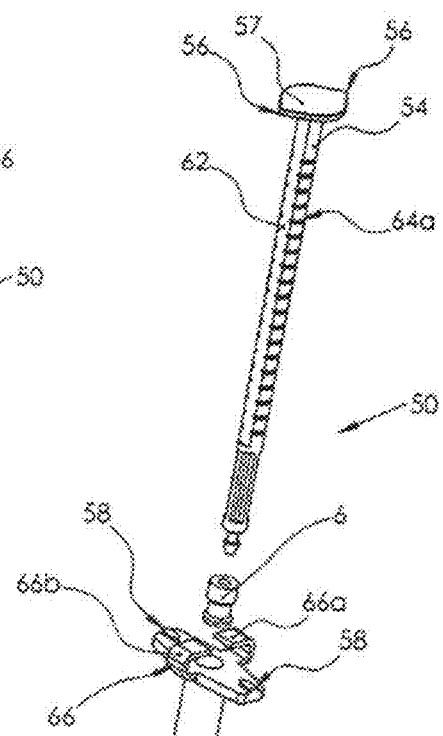
FIG. 34 is an exploded perspective view of the fluid dispensing device in the position of FIG. 31.
Figure 33:
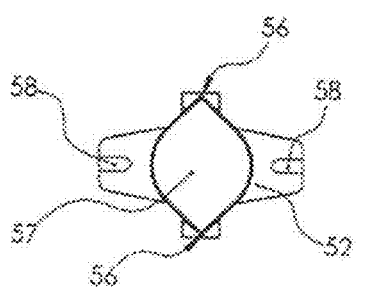
FIG. 33 is a top view of the fluid dispensing device in the position of FIG. 31.

The flexible structure 46 differs from flexible structure 24 of FIGS. 8-13 due to the mounting to the barrel 42. More specifically, arms 44a, 44b extend from support 44 which provides a snap attachment as flexible tabs or snapping grips 48, spaced apart by about 180 degrees to be formed on opposing sides of the support 44, are snapped over proximal flange 43 of barrel 42 and engage an undersurface of flange 43 as shown in FIGS. 22 and 23 in the same manner as in FIGS. 17 and 18 to attach flexible structure 46 to the barrel 42. (Note additional spaced tabs could also be provided).

The arms 44a, 44b, by engaging a groove of the plurality of grooves 12 provide a tactile and/or audible indicator of the movement and position of the plunger 4 in the same manner as described above with respect to the embodiment of FIG. 1, i.e., engagement of the arms 44a, 44b with grooves 12. Therefore, for brevity, further discussion of the arm/groove engagement and use of the fluid dispensing device of FIGS. 19-24 will not be provided since the discussion of the arm/groove engagement, the tactile and audible feedback and the use of the device 11 of the embodiment of FIG. 1 is fully applicable to fluid dispensing device 41 of FIGS. 19-24. Additionally, discussion above of adjustment of the distances between grooves and adjustment of the force to adjust the tactile feedback is fully applicable to the embodiment of FIGS. 19-24.

It should be appreciated that it is contemplated that the flexible structure 46 be attached to the barrel 42 during manufacture. However, it is also contemplated that in certain embodiments the user or clinician (e.g., pharmacist) post manufacture can snap fit (or otherwise attach) the flexible structure 46 to the barrel 42 if desired to provide better controlled incremental advancement. In such use, the user would remove from the package the flexible structure 46 and if desired attach flexible structure 46 by pressing the structure over the proximal end of the barrel 42 until the tabs 48 bypass and snap under flange 43. Thus, as in the embodiment of FIG. 14, a kit containing the plunger, barrel and mounting structure can be provided.

FIGS. 25-36 illustrate an alternate embodiment of the fluid dispensing device (syringe) wherein the user has the option to select either a) the incremental injection of fluid and feedback mechanism as in the aforedescribed embodiments; or b) smooth continuous injection without an arm/groove engagement as in a standard syringe. This is achieved by providing a plunger with grooves extending along only a portion of the circumference so that the arms of the flexible structure are not always engageable with the grooves.

More specifically, the fluid dispensing device (syringe) of FIGS. 25-36 is designated generally by reference numeral 51 and includes a barrel 52, a plunger 54 and a feedback mechanism 50. Penetrating needle 55 extends distally from a distal end of the barrel 52 in the same manner as needle 14 of FIG. 1. The barrel 52 includes a lumen formed therein to receive fluid for delivering to a patient and external markings 52a formed along its entire, or alternatively its partial, length to provide a visual indication to the user of the amount of fluid contained within the barrel 52. The plunger 54 is received in barrel 52 for axially slidable movement distally to dispense the fluid from the barrel 52. A seal 6 identical to seal 6 of FIG. 1 can be positioned in a proximal portion of barrel 52. The fluid dispensing device 51 has two positions: 1) an engagement position wherein the flexible structure 66 of the feedback mechanism 50 engages plunger grooves 64; and 2) a non-engagement position wherein the flexible structure 66 does not engage the plunger grooves 64. These two positions are determined by the rotational position of the plunger 54 relative to the barrel 52 as discussed in detail below. In the engagement position, a tactile and/or audible feedback is provided.

More specifically, plunger 54 has a cross-sectional configuration with two opposing curved walls 65a, 65b and two opposing flat walls 67a, 67b, with each flat wall 67a, 67b joining curved walls 65a, 65b on opposing sides (see the cross-sectional view of FIG. 29). Formed within the curved walls 65a, 65b are a plurality of grooves 64. A first set of grooves 64a are formed in an outer (external) surface of the wall 65a and a second set of grooves 64b are formed in an outer (external) surface of the wall 65b, a groove from one set radially aligned with a groove from the other set for engagement by the arms of the flexible structure 66. (Collectively grooves 64a and 64b are referred to as grooves 64). The grooves 64 extend along the length of the curved walls 65a, 65b, spaced apart at intervals or increments corresponding to the amount of fluid desired to be injected at each step of advancement of the plunger 54 within the barrel 52 in the same manner as described above. By placing the plunger grooves 64 on portions of the surface of the plunger 54 so they are radially spaced, the flats 67a, 67b provide a gap to which the arms 66a, 66b of the flexible structure 66 do not engage. Thus, the rotational position of the plunger 54 with respect to barrel 52 will determine if the feedback mechanism is engageable (operational) or not engageable (not operational). Consequently, the user can select whether detectible/measurable incremental advancement (with tactile and/or audible feedback) is desirable. It should be appreciated that the flats 67a, 67b are formed to provide a reduced cross-sectional diameter (transverse) region to provide a gap between the flexible arms 66a, 66b and plunger 54. Therefore, as can be appreciated, other plunger configurations other than flats are also contemplated, such as an oval cross-section, for example, to provide a reduced cross sectional dimension along a minor diameter for non-engagement of the arms and grooves and a larger cross-sectional diameter along a major diameter for engagement of the arms with the grooves.

In the illustrated embodiment, the plunger grooves 64 are equidistantly spaced apart to provide equal doses of fluid. However, it is also contemplated that in alternate embodiments, the spacing between grooves could be non-uniform to accommodate situations where it is desired to provide larger or smaller doses at certain times during injection. Also, the distances between the grooves can be greater or less than the distances shown in the Figures to provide variations on dosage delivery. Note that such variations are applicable to the grooves of each of the embodiments disclosed herein. Also note the grooves of each set are radially aligned due to the radial alignment of the tips of the arms 66a, 66b. If the tips are not radially aligned, then the grooves of each set would also not be radially aligned in order to accommodate the tips.

Figure 16:
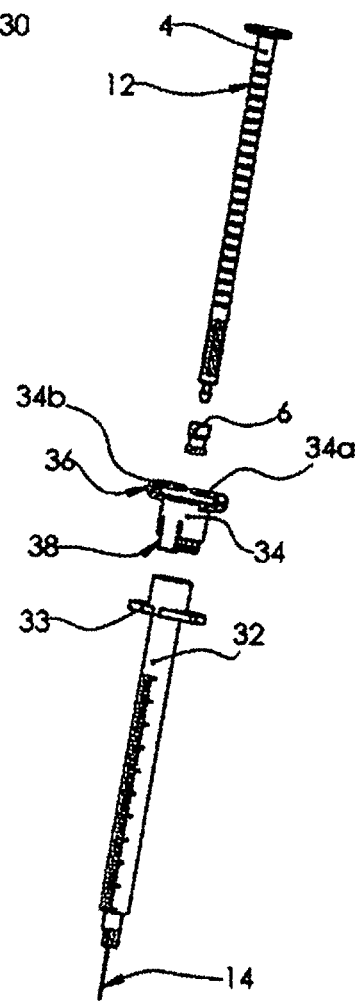
FIG. 16 is an exploded perspective view of the fluid dispensing device of FIG. 14.

Turning to the feedback mechanism 50 of device 51, the feedback mechanism includes a flexible structure 66 identical to flexible structure 13 of FIG. 3. That is, the flexible structure 66 includes a pair of flexible arms 66a, 66b having a somewhat U-shaped configuration with the proximal legs of the U extending inwardly toward the longitudinal axis and toward each other. For brevity, further discussion of the flexible structure construction and attachment to barrel 52 is not provided herein as the discussion of the construction and attachment of flexible structure 13, including its variations such as being mountable to the barrel as in FIG. 16, is fully applicable to the embodiment of FIGS. 25-36.

It should be appreciated that flexible structure 66 is one example of a flexible structure and feedback mechanism that can be used with the dispensing device 51 of FIGS. 25-36. The various flexible structures described herein such as structure 24 of FIGS. 8-13, or other flexible structures configured to engage the plunger grooves can also be utilized to selectively engage or not engage the grooves.

Plunger 54 has an end cap or pressing surface (or button) 57 at a proximal end having two opposing alignment (position) tabs 56, also referred to as alignment (position) indicators, on opposing sides of the cap 57 to indicate the rotational position of the plunger. Flexible structure 66 includes opposing alignment (position) tabs 58, also referred to as alignment (position) indicators, on opposing sides of an upper surface thereof, cooperating with position tabs 56 of plunger 54. When the tabs 56 of end cap 57 are longitudinally aligned with tabs 58 of flexible structure 66 on barrel 52 as in FIGS. 25-30, referred to herein as the aligned position, the arms 66a, 66b of the flexible structure 66 of the feedback mechanism 60 are engageable with the plunger grooves 64 of plunger 54. On the other hand, when the tabs 56 are not aligned (out of phase) with tabs 58, referred to herein as the non-aligned position, the arms 66a, 66b are not engageable with the plunger grooves 64 as shown in FIGS. 31-36. This occurs when the plunger 54 is rotated 90 degrees from the aligned position, and can be understood by comparing the position shown in FIGS. 27 and 28 to the position shown in FIGS. 33 and 34. In this non-aligned position, the arms 66a, 66b are no longer aligned with the curved walls 65a, 65b but instead are aligned (oppose) with the flat walls 67a, 67b of the plunger 54 and therefore, due to the reduced diameter, a gap is formed (see FIG. 36) and the arms 66a, 66b do not engage the walls 67a, 67b and allow for continuous smooth motion of the plunger 64 to inject the fluid from the barrel. It should be appreciated that FIGS. 25-36 show an example of an alignment indicator to indicate the rotational position of the plunger 54 relative to barrel 52. Other indicators on the plunger and/or flexible structure/barrel to inform the user of the rotational position of the plunger relative to the barrel 52 are also contemplated.

In addition, in alternate embodiments, instead of rotational movement of the plunger 54 to determine arm/groove engagement, the flexible structure can be rotated or repositioned or otherwise adjusted to move the flexible arms into or out of alignment with the plunger grooves to provide the user with the option of engaging the feedback mechanism.

Turning now to the use of fluid dispensing device 51, if the user decides to utilize the feedback mechanism 60 for controlled measured dispensing of fluid from the fluid dispensing device 51 by incremental advancement of plunger 54 as indicated by the tactile and/or audible indicator, the plunger 54 is positioned so that position tabs 56 are aligned with the position tabs 58 on the flexible structure 66 on barrel 52. With such alignment, when plunger 54 is advanced through the lumen of the barrel 52, the plunger grooves 64 are engaged by the flexible arms 66a, 66b in the arm/groove engagement manner discussed above. This is because when aligned, the curved walls 65a, 65b containing the grooves 64 are aligned with the ends (tips) of the proximal legs of the arms 66a, 66b. If the user does not wish to engage the feedback mechanism 60 and desires smooth continuous injection, the user rotates the plunger 54, e.g., 90 degrees in either direction, to the position of FIGS. 33 and 34 so that position tabs 56 on plunger 54 are not aligned with position tabs 58 on the flexible structure 66. This is because in this non-aligned position, the flat walls 67a, 67b not containing the grooves 64 are aligned with the ends (tips) of the proximal legs of the arms 66a, 66b and are not engaged by the legs. Note the fluid dispensing device can be provided, e.g., packaged, with the plunger 54 in the position of FIG. 25 or in the position of FIG. 31, and the user would determine the necessity of rotation depending on its intended use.

It is contemplated that the user can adjust the rotational position of plunger 54 before initiation of injection of fluid as well as during the injection. For example, if the user wishes to initially provide small injections of the fluid (with the tactile and/or audible feedback) but then wants to inject a continuous dose, the user can rotate the plunger 54 as described above to move the grooves 64 out of alignment with the arms 66a, 66b. If incremental injections are then desired, the plunger can be rotated back to the aligned position so the arms 66a, 66b are aligned with grooves 64. This rotation to engaged and non-engaged positions can be repeated multiple times if desired.

The flexible structure 66 of FIGS. 25-36 is shown by way of example as it should be appreciated that the other flexible structures disclosed herein, e.g., flexible structure 24 of FIGS. 8-13, can be utilized with the rotational plunger embodiment of FIGS. 25-36. Additionally, other flexible structures to interact with the plunger grooves can also be utilized.

In the alternate embodiment of FIGS. 40-47, the plunger 82 is rotatable to change its orientation in the same manner as plunger 54 of fluid dispensing device 51 of FIG. 25. However, in this embodiment, the plunger 82 is rotatable to change the increments of advancement of the plunger 82. More specifically, plunger 82 has a first set of grooves 84 on opposing walls and a second set of grooves 85 on opposing walls. The grooves 84, 85 extend along a length (either the entire or partial length) of the walls of the plunger 82. A radial gap is provided between the grooves to separate the grooves. Each of the grooves 84 of the first set of grooves 84 are spaced apart a first distance L 1 and each of the grooves 85 of the second set of grooves 85 are spaced apart a second distance L2. As shown, distance L2 is greater than distance L1 so that the plunger 82 moves in larger increments when grooves 85 are engaged than when grooves 84 are engaged. The plunger 82 can have the first set of grooves 84 on one curved surface and the second set of grooves on an opposing curved surface, with a gap between the grooves 84, 85. Consequently, in the embodiment of FIGS. 40-47, the user has the option to select either a) the smaller incremental injection of fluid with the accompanying tactile and/or audible feedback as shown in FIG. 46 or b) a larger incremental injection of fluid with the accompanying tactile and/or audible feedback as shown in FIG. 47. Thus, the rotational position of the plunger 82 with respect to barrel 52 will determine which grooves are engageable. Thus, the user can select which detectible/measurable incremental advancement is desirable with its accompanying tactile (and audible) feedback.

Figure 40:
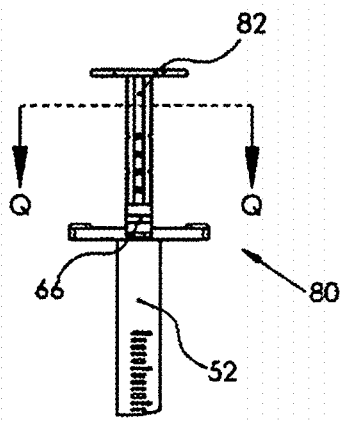
FIG. 40 is a front view of a proximal portion of another alternate embodiment of the fluid dispensing device of the present invention.
Figure 41:
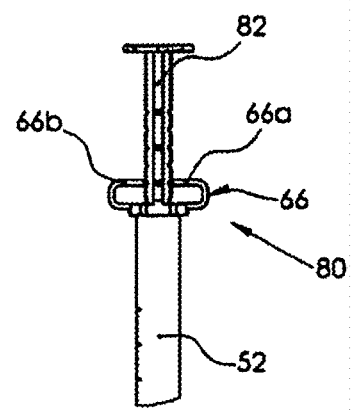
FIG. 41 is a side view of the fluid dispensing device of FIG. 40.
Figure 43:
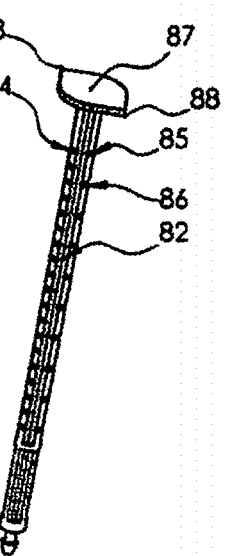
FIG. 43 is a perspective view of the plunger of the fluid dispensing device of FIG. 40.

In all other respects, the fluid dispensing device of FIGS. 40-47 is identical to fluid dispensing 11 of FIGS. 1-6. The fluid dispensing device (syringe) of FIGS. 40-47 includes a barrel 52 (only a portion of which is shown) identical to barrel 52 of the embodiment of FIG. 25, a plunger 82 and a feedback mechanism 80. Feedback mechanism includes a flexible structure 66 with arms 66a, 66b identical to flexible structure 66 of FIG. 25 (and FIG. 1). That is, the flexible structure 66 includes a pair of flexible arms 66a, 66b having a somewhat U-shaped configuration with the proximal legs of the U extending inwardly toward the longitudinal axis and toward each other. For brevity, further discussion of the flexible structure construction and attachment to barrel 52 is not provided herein as the discussion of the construction and attachment of flexible structure 66 of FIG. 25, including its variations, is fully applicable to the embodiment of FIGS. 40-47. Note only a proximal region of the barrel is illustrated in FIGS. 40 and 41 since the barrel 52 of these Figures is identical to the barrel 52 of FIG. 25.

It should be appreciated that flexible structure 66 is one example of a flexible structure and feedback mechanism that can be used with the groove selection device of FIGS. 40-47. The other flexible structures described herein such as structure 24 of FIGS. 8-13, or other flexible structures, can also be utilized.

A penetrating needle (not shown) extends distally from a distal end of the barrel 52 of FIGS. 40 and 41 in the same manner as needle 14 of FIG. 1. The barrel 52, like the barrel 52 of FIG. 25, includes a lumen formed therein to receive fluid for delivering to a patient and external markings formed along its length to provide a visual indication to the user of the amount of fluid contained within the barrel, and the plunger 82 is received in the barrel for axially slidable movement distally to dispense the fluid from the barrel 52 in the manner described above. A seal identical to seal 6 of FIG. 1 can be provided. As noted above, the fluid dispensing device of FIGS. 40-47 has two positions: 1) a first position wherein the flexible structure 66 of the feedback mechanism 80 engages plunger grooves 84 (see FIGS. 46); and 2) a second position wherein the flexible structure 66 of the feedback mechanism engages the plunger grooves 85 (see FIG. 47). These two positions are determined by the rotational position of the plunger 84 relative to the barrel 52. In both positions, a tactile and/or audible feedback is provided.

Figure 42:
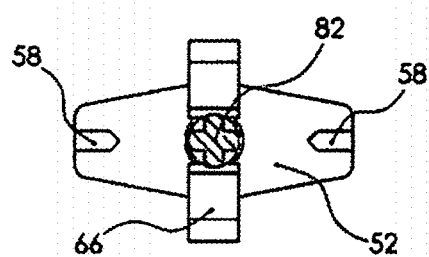
FIG. 42 is a top view of the fluid dispensing device of FIG. 40.

To accommodate these two positions, the plunger 82 has a transverse cross-sectional dimension as shown in FIG. 42 with grooves 84 on the curved walls along one axis of the cross and grooves 85 on the curved walls along another axis of the cross, the two axes being perpendicular.

Figure 36:
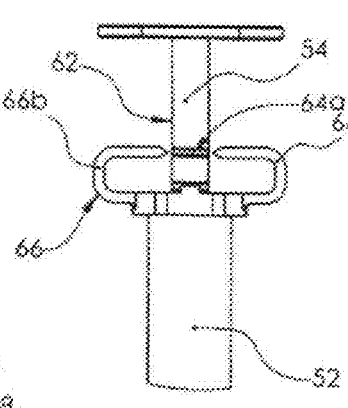
FIG. 36 is a detailed view of the indicated area M of FIG. 32.
Figure 35:
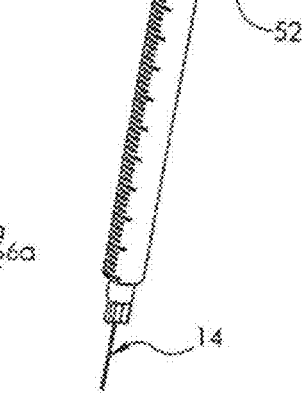
FIG. 35 is a cross-sectional view taken along line N-N of FIG. 31.

Further, in some embodiments, the plunger 82 can have flat walls or other reduced diameter feature between the curved walls containing grooves 84 and 85 to provide a disengaged position of the plunger grooves and arms of the flexible structure to provide a continuous motion as in a standard syringe (as in the flat walls of FIGS. 35 and 36). Thus, the user would have a third option (a third rotational position of the plunger) to bypass the feedback mechanism as in the embodiment of FIGS. 25-36 wherein a gap is formed between the flexible arms and flat walls so that the arms of the flexible structure would not engage the plunger. The plunger would have a cross-sectional dimension to accommodate these three positions.

Additionally, the plunger can have sets of grooves with spacing different than spacing L1, L2 of grooves 84, 85.

In the illustrated embodiment, the plunger grooves 84 and plunger grooves 85 are equidistantly spaced apart to provide equal doses of fluid. However, it is also contemplated that in alternate embodiments, the spacing between grooves could be non-uniform to accommodate situations where it is desired to provide larger or smaller doses at certain times during injection. Also, the distances between the grooves can be greater or less than the distances shown in the Figures to provide variations on dosage delivery. An example of spacing can be 0.1 cc, 0.25 cc, 0.50 cc, etc. Note that such variations are applicable to the grooves of each of the embodiments disclosed herein.

Plunger 82 has an end cap or pressing surface (or button) 87 at a proximal end having two opposing alignment (position) tabs or alignment (position) indicators 88 on opposing sides of the cap 87 to indicate the rotational position of the plunger. Flexible structure 66 includes opposing alignment (position) tabs 58, on opposing sides of an upper surface of the flexible structure, cooperating with position tabs 88 of plunger 82. When the tabs 88 are longitudinally aligned with tabs 58 as in FIGS. 44 and 46, the arms 66a, 66b of the flexible structure 66 of the feedback mechanism 60 are engageable with the plunger grooves 84. On the other hand, when the tabs 88 are not aligned with tabs 58, i.e., are out of phase with tabs 58, the arms 66a, 66b are engageable with the plunger grooves 85 as shown in FIGS. 45 and 47. This occurs when the plunger 82 is rotated 90 degrees from the position shown in FIGS. 44 and 46 to the position shown in FIGS. 45 and 47. Note an alignment tab can also be provided to indicate the position of FIGS. 45 and 47. It should be appreciated that FIGS. 40-47 show an example of an alignment indicator to indicate the position of the plunger 82 relative to barrel 52. Other indicators to inform the user of the rotational position of the plunger relative to the barrel 52 are also contemplated. For example, the plunger cap can be pad printed to indicate its pitch (or for the embodiment of FIG. 25 to indicate engaged or non-engaged positions).

The configuration of the grooves 84 and 85 could differ to provide a different tactile feel and/or different audible feedback, i.e., engagement of the arms of the flexible structure of one set of grooves being louder than engagement with the other set of grooves, or one set of grooves providing more resistance than the other set of grooves to facilitate the user differentiating between which set of grooves are engaged. The various ways to adjust the force required to advance the plunger discussed above are fully applicable to the embodiment of FIGS. 40-47 as well as to the other embodiments described herein.

In use, if the user desires incremental advancement of the plunger 82 for controlled measured dispensing of fluid from the syringe in accordance with the groove distances L1, the plunger 82 is positioned so that position tabs 88 are aligned with the position tabs 58 on the flexible structure 66 on barrel 52. With such alignment, when plunger 82 is advanced through the lumen of the barrel, the plunger grooves 84 are engaged by the flexible arms 66a, 66b in the arm/groove engagement manner discussed above. This is because when aligned, the curved walls containing the grooves 84 are aligned with the ends of the proximal legs of the arms 66a, 66b. If the user desires incremental advancement of the plunger for controlled measured dispensing of fluid from the syringe in accordance with the groove distances L2 to provide larger dosages, the user rotates the plunger 82, e.g., 90 degrees in either direction, to the position of FIGS. 45 and 47 so that position tabs 88 are not aligned with tabs 58. In this position, when not aligned, the grooves 85 are aligned with the ends of the proximal legs of the arms 66a, 66b. Note the device can be provided with the plunger in the position of FIG. 46 or in the position of FIG. 47, and the user would determine the necessity of rotation depending on its intended use.

It is contemplated that the user can adjust the rotational position of plunger 82 before initiation of injection of fluid as well as during the injection. For example, if the user wishes to initially provide small injections of the fluid but then wants to inject a dose or doses of greater increments, the user can rotate the plunger 82 as described above to move the grooves 85 into alignment with the arm 66a, 66b. If smaller injections are then desired, the plunger 82 can be rotated back to the position so the arms 66a, 66b are aligned with grooves 84. This rotation between the two engaged positions can be repeated multiple times if desired.

The flexible structure 66 of FIGS. 40-47 is shown by way of example as it should be appreciated that the other flexible structures disclosed herein, e.g., flexible structure 24, can be utilized with the rotational plunger embodiment of FIGS. 40-47. Additionally, other flexible structures to interact with the plunger grooves can also be utilized.

In addition, in alternate embodiments, instead of rotational movement of the plunger 54 to determine arm/groove engagement, the flexible structure can be selectively rotated or repositioned or otherwise adjusted to move the flexible arms into or out of alignment with the plunger grooves to provide the user with the selective engagement of the desired feedback mechanism.

It is also contemplated that the feedback mechanism of FIGS. 40-47 can be mountable to the barrel 52 in the same manner as in the embodiment of FIG. 16.

FIGS. 37-47 illustrate an embodiment where different spacing of grooves provides delivery of different increments and accompanying feedback. In another concept, rather than relying on rotation/reorientation of the plunger to provide the desired dosage indicator, the flexible structure is configured to provide such differentiation. For example, one of the arms of the flexible structure can have a first flexibility and the other arm can have a second flexibility. In this manner, the tactile feel and audible click will also be different as one ratchet arm would be stiffer and louder than the other to allow differentiation between them. For example, assuming x units, e.g., 37 units, are required to be administered. The smaller distance L1 can represent delivery of 1 unit increments and the larger distance L2 could represent 5 unit increments. As the plunger is advanced, the user would hear and feel the 1 unit increments but also feel the 5 mm increments since the flexible structure engagement with the grooves would differ. In this way, the 5 mm increment ratchet would facilitate the user's count of the administered dose. Note that the number of units and the increments are provided by way of example as a different number of units and different increments are also contemplated.

It is also contemplated that in any of the embodiments disclosed herein, instead of two or more sets of grooves, a single set of grooves can be provided that has variable feedback depending on groove configuration. For example, every $5^{th}$ or $10^{th}$ groove can be different, e.g., have a greater depth, so that every $5^{th}$ or $10^{th}$ click produces a different feedback than the other grooves to simplify counting when a large number of clicks is provided. Note that $5^{th}$ and $10^{th}$ are used by way of example since other grooves, e.g., $3^{rd}$, could be modified to provide varying feedback at desired intervals.

Figure 53:
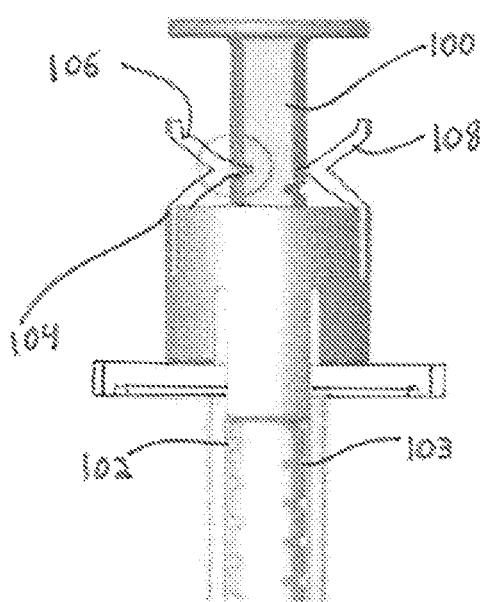
FIG. 53 is a side view of a proximal portion of a fluid dispensing device of an alternate embodiment.
Figure 54:
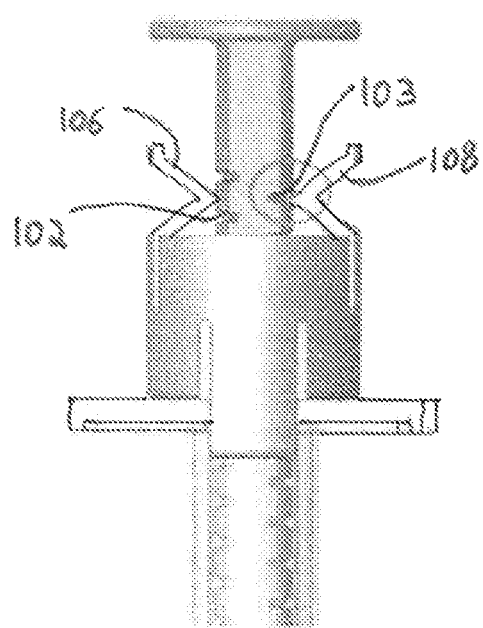
FIG. 54 is a side view similar to FIG. 53 showing the plunger further advanced into the barrel.

In an alternate embodiment illustrated in FIGS. 53 and 54, a multi-ratchet configuration can be provided. If the desired increments to be applied are sufficiently small that it is difficult to attain with a single ratchet, a ratchet could be provided on each side of the barrel and the plunger could have a first set of grooves separated by a distance X and a second set of grooves separated by a distance X, with the grooves offset so that one ratchet would engage one set of grooves and the other ratchet would engage the other set of grooves. By way of example, the grooves can be separated by a distance of 2 mm and have an offset of 1 mm so that 1 mm increments can be attained. As shown, plunger 100 has a first set of grooves 102 and a second set of grooves 103 longitudinally offset. In FIG. 52, arm 106 of deflectable structure 104 engages a groove of the first set of grooves 102 and arm 108 is not engaged with a groove of the second set of grooves 103. When the plunger 100 is further advanced to the position of FIG. 53, arm 106 of deflectable structure 104 does not engage a groove of the first set of grooves 102 and arm 108 engages a groove of the second set of grooves 103. This enables tiny injections to be applied since the minimum spacing of the grooves is limited by a minimum depth/height of a groove necessary to provide detectable feedback, and such offset allows for sufficiently sized grooves in minimally spaced increments along the plunger. Note any of the foregoing deflectable structures, including the mountable structures, can be utilized with the embodiment of FIGS. 53 and 54. Additionally, the first and second sets of grooves could have different spacing between the grooves.

In another alternate embodiment, a plunger cross-shaped in transverse cross-section could have grooves of different spacing on each of the four wings (walls). By way of example, the wings could have increments corresponding to 0.1, 0.2. 0.25 and 0.5 cc. Note that other increments are also contemplated, the foregoing provided by way of example. Each wing would be pad-printed to indicate its pitch. The snap on attachment, i.e., the attachable flexible (mounting) structure would have an orientation feature so that its flexible arm would be set to engage with a single wing. One way this can be achieved is by providing the plunger with a cross-shaped cross section, or other asymmetrical cross-section, wherein each wing of the cross has a slightly different dimension or configuration. The flexible structure has an opening conforming to the wing shape and thus could only be placed in a single orientation. In this manner, a user would select the modular flexible structure for the desired orientation and attach the flexible structure to the barrel so that the flexible arm is oriented to engage only the grooves on the selected wing of the cross-shaped plunger. Thus, the assembler of the syringe would select the flexible structure from a set of flexible structures and mount it to the barrel so its flexible arm engages the desired wing of the plunger for administering the desired fluid increments. Note that the assembler of the various embodiments of the syringes disclosed herein could be by the manufacturer who would mount the modular flexible structures to barrels in various orientations to provide assembled syringes with select dosage increments. The assembler of the various embodiments of the syringes disclosed herein could also be the hospital pharmacist who can customize the syringes by orientation of the flexible structures received from the manufacturer.

In alternate embodiments, the flexible structure of any of the embodiments disclosed herein can be removably mounted to the barrel so the user can remove it from the barrel to disengage the feedback mechanism and controlled incremental advancement.

It should be appreciated that the flexible structures/groove engagement disclosed herein provide one form of ratchet to provide the feedback mechanisms. Other flexible structures and arm configurations to perform the ratcheting function are also contemplated.

It should also be appreciated that although the grooves of the foregoing embodiments are located on the plunger and the flexible engaging elements are attached or extend from the barrel, it is also contemplated in any of the foregoing embodiments that the groove/flexible element arrangement is reversed so that the flexible element is on the plunger and extends transversely therefrom and the barrel has one or more sets of grooves along part of or along its entire length. In this way, as the plunger is advanced within the barrel, the flexible elements of the plunger will engage the various grooves of the barrel and provide the incremental doses and the tactile and/or audible indication in the same manner as the when the plunger has the grooves and the barrel has the flexible elements as described in detail above. Instead of grooves, the barrel can have a rigid structure engaging the flexible elements of the plunger.

FIGS. 48-52 provide one example of an arrangement wherein plunger 90 has the flexible elements and the barrel has the rigid element (s). More specifically, plunger 90 has flexible lips or ribs axially spaced around the circumferential surface of plunger 90. Barrel 94 has a lip structure 96 and ribs 98 which make lip structure non-flexible (rigid). When flexible lips 92 engage with the rigid structure 96 they provide a tactile and/or audible feedback to the user. Note that the outside diameter of the lips 92 is preferably smaller than the inner diameter of the barrel 94 to avoid additional frictional resistance during movement of the plunger 90 within the barrel 92.

The pressing surface of the plungers disclosed herein could have different configurations such as a small flat button, a finger ring or a large surface button to ergonomically accommodate clinical applications that require exertion of higher pressure. In some embodiments, such pressing surface can be a snap on button which can be non-removably attached to the plunger, or alternatively, removably attached to the plunger, during manufacture or by a user. This would facilitate assembly as the flexible structure could be placed on the barrel after the syringe is positioned in the barrel. For example, the hospital pharmacist would receive from the manufacturer the plunger positioned in the barrel and a separate flexible structure and pressing surface. The pharmacist could select the desired flexible structure for the desired orientation of the flexible structure and slide it over the plunger and onto the barrel for snap fitting onto the barrel. The pressing surface (cap) for the plunger could then be applied.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A fluid dispensing device comprising:
a barrel having a lumen for containing a fluid therein and a flexible structure extending from the barrel; and
a plunger axially slidable within the lumen to dispense fluid from the barrel, the plunger having a first set of axially spaced apart grooves and a second set of axially spaced apart grooves, the first set of grooves radially spaced from the second set of grooves, and a wall extending longitudinally between the first and second sets of grooves, and
the flexible structure including at least one flexible arm extending transversely with respect to the barrel, the flexible structure positioned to engage the first set of grooves and the second set of grooves, the plunger rotatable relative to the barrel to move the plunger from a first orientation to a second orientation without changing the axial orientation of the plunger wherein a) in the first orientation the flexible structure is engageable with the first set of grooves and the second set of grooves when the plunger is advanced axially within the barrel and b) in the second orientation the flexible structure is not engageable with the first set of grooves or the second set of grooves and is aligned with the longitudinally extending wall when the plunger is advanced axially through the barrel.

2. The device of claim 1, wherein the flexible structure is selectively mountable to the barrel.

3. The device of claim 2, wherein in the first orientation the plunger is advanced through the barrel to dispense first increments of fluid and in the second orientation the plunger is advanced through the barrel to continuously dispense fluid different than in the first increments.

4. The device of claim 1, wherein the plunger has has a first curved wall and a second curved wall, the first set of grooves formed on the first wall and the second set of grooves formed on the second wall, and the longitudinally extending wall is a flat wall.

5. The device of claim 1, wherein the flexible structure is snapped onto the barrel.

6. The device of claim 1, wherein the flexible structure has an indicator to indicate the rotational position of the plunger to indicate whether the first set of grooves and the second set of grooves are engaged by the flexible structure or the first set of grooves and second set of grooves are not engaged by the flexible structure.

7. The device of claim 1, wherein engagement of the flexible structure with one of the grooves provides one or both of a tactile indication and audible indication to a user.

8. The device of claim 1, wherein engagement with of the flexible structure with the first set of grooves provides a first feedback and engagement of the flexible structure with the second set of grooves provides a second feedback more prominent than the first feedback.

9. The device of claim 1, wherein the flexible structure includes a pair of transversely extending flexible arms, the flexible arms engageable with the grooves, the first arm having a first stiffness to provide the first feedback and the second arm having a second stiffness to provide the second feedback.

* * * * *